US010969370B2

United States Patent
Lagowski et al.

(10) Patent No.: US 10,969,370 B2
(45) Date of Patent: Apr. 6, 2021

(54) MEASURING SEMICONDUCTOR DOPING USING CONSTANT SURFACE POTENTIAL CORONA CHARGING

(71) Applicant: SEMILAB Semiconductor Physics Laboratory Co., Ltd., Budapest (HU)

(72) Inventors: Jacek Lagowski, Tampa, FL (US); Marshall Wilson, Tampa, FL (US); Alexandre Savtchouk, Tampa, FL (US); Carlos Almeida, Tampa, FL (US); Csaba Buday, Balatonalmádi (HU)

(73) Assignee: SEMILAB Semiconductor Physics Laboratory Co., Ltd., Budapest (HU)

( * ) Notice: Subject to any disclaimer, the term of this patent is extended or adjusted under 35 U.S.C. 154(b) by 1200 days.

(21) Appl. No.: 14/731,677

(22) Filed: Jun. 5, 2015

(65) Prior Publication Data
US 2016/0356750 A1    Dec. 8, 2016

(51) Int. Cl.
*G01N 33/00* (2006.01)
*G01R 29/12* (2006.01)
*G01N 27/22* (2006.01)

(52) U.S. Cl.
CPC .......... *G01N 33/00* (2013.01); *G01N 27/221* (2013.01); *G01R 29/12* (2013.01); *G01N 2033/0095* (2013.01)

(58) Field of Classification Search
None
See application file for complete search history.

(56) References Cited

U.S. PATENT DOCUMENTS

| 4,812,756 A | * | 3/1989 | Curtis | G01R 15/165 |
| | | | | 250/492.2 |
| 5,216,362 A | * | 6/1993 | Verkuil | G01R 31/2831 |
| | | | | 250/492.2 |

(Continued)

FOREIGN PATENT DOCUMENTS

| JP | S64-69024 | 3/1989 |
| JP | H05-206243 A | 8/1993 |
| JP | H08-236591 | 9/1996 |

OTHER PUBLICATIONS

Wikipedia Entry for Capacitance (Year: 2019).*
(Continued)

*Primary Examiner* — Catherine T. Rastovski
*Assistant Examiner* — Leonard S Liang
(74) *Attorney, Agent, or Firm* — Fish & Richardson P.C.

(57) ABSTRACT

An example method of characterizing a semiconductor sample includes measuring an initial value, $V_{in}$, of a surface potential at a region of a surface of the semiconductor sample, biasing the semiconductor sample to have a target surface potential value ($V_0$) of 2V or less, and depositing a monitored amount of corona charge ($\Delta Q_1$) on the region of the surface after adjusting the surface potential to the target value. The method also includes measuring a first value, $V_1$, of the surface potential at the region after depositing the corona charge, determining the first change of surface potential ($\Delta V_1 = V_1 - V_0$), and determining the first capacitance value $C_1 = \Delta Q_1/\Delta V_1$, and characterizing the semiconductor sample based on $V_0$, $V_1$, $\Delta V_1$, $\Delta Q_1$ and $C_1$.

18 Claims, 9 Drawing Sheets

(56) References Cited

U.S. PATENT DOCUMENTS

| | | | | |
|---|---|---|---|---|
| 5,485,091 A * | 1/1996 | Verkuil | G01R 31/2831 | 324/455 |
| 5,498,974 A * | 3/1996 | Verkuil | G01R 31/2648 | 250/492.2 |
| 5,639,357 A * | 6/1997 | Xu | H01L 21/32115 | 204/192.12 |
| 5,644,223 A | 7/1997 | Verkuil | | |
| 5,773,989 A * | 6/1998 | Edelman | G01N 27/60 | 257/E21.531 |
| 5,807,467 A * | 9/1998 | Givens | C23C 14/34 | 204/192.12 |
| 5,963,783 A * | 10/1999 | Lowell | H01L 21/02112 | 257/E21.279 |
| 6,011,404 A * | 1/2000 | Ma | G01R 31/265 | 257/E21.531 |
| 6,034,535 A * | 3/2000 | Liberman | G01R 31/2648 | 324/658 |
| 6,037,797 A * | 3/2000 | Lagowski | G01R 31/2648 | 324/754.05 |
| 6,051,121 A * | 4/2000 | Givens | C23C 14/34 | 204/298.06 |
| 6,097,196 A * | 8/2000 | Verkuil | G01R 31/2648 | 250/492.2 |
| 6,097,205 A * | 8/2000 | Liberman | G01R 31/2648 | 324/662 |
| 6,127,289 A * | 10/2000 | Debusk | H01L 21/326 | 257/E21.327 |
| 6,191,605 B1 * | 2/2001 | Miller | G01R 29/24 | 324/762.07 |
| 6,267,852 B1 * | 7/2001 | Givens | C23C 14/34 | 204/192.12 |
| 6,335,630 B2 * | 1/2002 | Miller | G01R 29/24 | 324/762.05 |
| 6,395,437 B1 * | 5/2002 | Wollesen | G01R 31/303 | 382/145 |
| 6,448,804 B2 * | 9/2002 | Miller | G01R 29/24 | 324/455 |
| 6,538,462 B1 * | 3/2003 | Lagowski | H01L 22/14 | 257/E21.531 |
| 6,569,691 B1 * | 5/2003 | Jastrzebski | H01L 22/14 | 257/E21.531 |
| 6,679,976 B2 * | 1/2004 | Baldwin | C23C 14/46 | 204/192.12 |
| 6,723,209 B2 * | 4/2004 | Baldwin | C23C 14/46 | 204/192.12 |
| 6,734,696 B2 * | 5/2004 | Horner | G01N 27/60 | 324/750.03 |
| 6,937,050 B1 * | 8/2005 | Fung | G01R 31/311 | 324/750.03 |
| 7,012,438 B1 * | 3/2006 | Miller | H01L 22/12 | 257/E21.53 |
| 7,103,848 B2 * | 9/2006 | Barsness | G06F 17/241 | 715/776 |
| 7,110,238 B1 * | 9/2006 | Xu | G01N 27/002 | 361/220 |
| 7,202,691 B2 * | 4/2007 | Lagowski | G01R 31/312 | 324/754.21 |
| 7,230,443 B1 * | 6/2007 | Fung | G01R 31/2648 | 324/762.05 |
| 7,316,764 B2 * | 1/2008 | Baldwin | C23C 14/46 | 204/192.32 |
| 7,335,315 B2 * | 2/2008 | Matsuda | H01L 21/67248 | 216/60 |
| 7,358,748 B1 | 4/2008 | Miller et al. | | |
| 7,405,580 B2 | 7/2008 | Marinskiy | | |
| 7,491,953 B2 * | 2/2009 | Horsky | H01J 37/08 | 250/298 |
| 7,521,946 B1 | 4/2009 | Janik | | |
| 7,538,333 B1 * | 5/2009 | Samsavar | G01R 31/303 | 250/492.1 |
| 7,663,385 B2 * | 2/2010 | Kamieniecki | G01R 31/2648 | 324/754.23 |
| 7,772,866 B2 * | 8/2010 | Patterson | H01L 22/34 | 324/750.3 |
| 7,893,703 B2 * | 2/2011 | Rzepiela | G01R 31/2831 | 324/754.24 |
| 7,960,709 B2 * | 6/2011 | Horsky | H01J 37/08 | 250/298 |
| 8,004,290 B1 * | 8/2011 | Zhang | G01R 31/129 | 324/671 |
| 8,071,958 B2 * | 12/2011 | Horsky | H01J 27/20 | 118/723 CB |
| 8,163,571 B2 * | 4/2012 | Jaeger | H01L 21/2855 | 257/E21.268 |
| 8,232,817 B2 * | 7/2012 | Kamieniecki | G01R 31/2656 | 324/754.23 |
| 8,410,459 B2 * | 4/2013 | Horsky | H01J 27/20 | 250/282 |
| 8,585,877 B2 * | 11/2013 | Jaeger | H01L 21/2855 | 118/712 |
| 8,618,514 B2 * | 12/2013 | Horsky | H01J 27/20 | 118/723 CB |
| 8,909,365 B2 * | 12/2014 | Valcore, Jr. | G01N 27/62 | 700/121 |
| 9,084,334 B1 * | 7/2015 | Gefter | H05F 3/06 | |
| 2001/0000651 A1 * | 5/2001 | Miller | G01R 29/24 | 324/762.05 |
| 2001/0014520 A1 * | 8/2001 | Usui | C23C 16/50 | 438/586 |
| 2002/0006740 A1 * | 1/2002 | Kamieniecki | H01L 22/10 | 438/795 |
| 2002/0008536 A1 * | 1/2002 | Miller | G01R 29/24 | 324/762.05 |
| 2002/0125900 A1 * | 9/2002 | Savtchouk | G01B 7/085 | 324/750.02 |
| 2002/0130674 A1 * | 9/2002 | Lagowski | G01B 7/085 | 324/750.02 |
| 2002/0189938 A1 * | 12/2002 | Baldwin | C23C 14/46 | 204/298.03 |
| 2003/0024807 A1 * | 2/2003 | Baldwin | C23C 14/46 | 204/192.12 |
| 2004/0019442 A1 * | 1/2004 | Kitajima | G01N 27/221 | 702/64 |
| 2004/0112764 A1 * | 6/2004 | Stokes | G01N 33/2841 | 205/782 |
| 2004/0191936 A1 * | 9/2004 | Tsidilkovski | H01J 37/3171 | 438/18 |
| 2004/0241890 A1 * | 12/2004 | Steele | G01N 27/002 | 438/14 |
| 2005/0006226 A1 * | 1/2005 | Baldwin | C23C 14/46 | 204/192.32 |
| 2005/0059174 A1 * | 3/2005 | Steele | G01N 27/002 | 438/14 |
| 2005/0174135 A1 * | 8/2005 | Matsuda | H01L 21/67248 | 216/60 |
| 2005/0196882 A1 * | 9/2005 | Steeples | G01R 31/2656 | 438/16 |
| 2005/0239224 A1 * | 10/2005 | Kitajima | G01B 11/065 | 438/16 |
| 2006/0097193 A1 * | 5/2006 | Horsky | H01J 37/08 | 250/492.21 |
| 2006/0267622 A1 * | 11/2006 | Lagowski | G01R 31/312 | 324/754.21 |
| 2007/0018674 A1 * | 1/2007 | Cho | G01R 31/312 | 324/754.03 |
| 2007/0069759 A1 * | 3/2007 | Rzepiela | G01R 31/2831 | 324/762.05 |
| 2007/0148795 A1 * | 6/2007 | Kitajima | G01N 27/221 | 438/14 |
| 2007/0181830 A1 * | 8/2007 | Horsky | H01J 27/20 | 250/492.21 |
| 2007/0194252 A1 * | 8/2007 | Horsky | H01J 37/08 | 250/492.21 |
| 2007/0273400 A1 * | 11/2007 | Kamieniecki | G01R 31/2648 | 324/754.23 |
| 2008/0174918 A1 * | 7/2008 | Kim | G11B 9/08 | 360/250 |

(56) References Cited

U.S. PATENT DOCUMENTS

| | | | | |
|---|---|---|---|---|
| 2008/0260398 A1* | 10/2008 | Itoh | G03G 15/5045 | 399/44 |
| 2008/0297189 A1* | 12/2008 | Everaert | G01R 31/2656 | 324/754.09 |
| 2008/0299681 A1* | 12/2008 | Jaeger | H01L 21/2855 | 438/8 |
| 2008/0305598 A1* | 12/2008 | Horsky | H01J 37/08 | 438/303 |
| 2009/0090872 A1* | 4/2009 | Horsky | H01J 27/20 | 250/427 |
| 2010/0008015 A1* | 1/2010 | Booth | H01L 21/6833 | 361/234 |
| 2010/0032587 A1* | 2/2010 | Hosch | H01J 37/06 | 250/492.3 |
| 2010/0060307 A1* | 3/2010 | Kamieniecki | G01R 31/2648 | 324/754.21 |
| 2011/0226969 A1* | 9/2011 | Horsky | H01J 27/20 | 250/492.21 |
| 2012/0076475 A1* | 3/2012 | Horsky | H01J 27/20 | 392/386 |
| 2012/0160415 A1* | 6/2012 | Jaeger | H01L 21/2855 | 156/345.24 |
| 2012/0176146 A1* | 7/2012 | Oborina | G01R 31/311 | 324/658 |
| 2012/0283973 A1* | 11/2012 | Samara | H01J 37/32935 | 702/65 |
| 2012/0321335 A1* | 12/2012 | Fujiwara | G03G 15/2078 | 399/69 |
| 2013/0068963 A1* | 3/2013 | Kireeff Covo | H01J 27/02 | 250/424 |
| 2013/0082241 A1* | 4/2013 | Kub | H01L 27/148 | 257/21 |
| 2013/0164665 A1* | 6/2013 | Ishii | G03G 9/08 | 430/105 |
| 2013/0257472 A1* | 10/2013 | Kamieniecki | H01L 22/14 | 324/762.01 |
| 2014/0061816 A1* | 3/2014 | Horsky | H01J 27/20 | 257/369 |
| 2014/0132286 A1* | 5/2014 | Oborina | G01R 31/311 | 324/658 |
| 2014/0147134 A1* | 5/2014 | Verheijen | G03G 15/0291 | 399/31 |
| 2015/0020972 A1* | 1/2015 | Jensen | H01J 37/32935 | 156/345.28 |
| 2015/0061714 A1* | 3/2015 | Kelly-Morgan | G01N 27/00 | 324/754.11 |
| 2015/0098161 A1* | 4/2015 | Horowy | H02H 9/02 | 361/87 |

OTHER PUBLICATIONS

"www.keithly.com applications guide: C-V Testing for Components and Semiconductor Devices" (Year: 2014).*

Czett, A. et al., Non-contact High Precision Alternative to Hg Probe for Dopant Profiling in SiC, Phys. Status Solidi C 11, pp. 1601-1605 (2013), DOI: 10, 1002/pssc201400057.

Marinskiy, D., et al., "A Novel Approach to Measuring Doping in SiC by Micro Spot Corona—Kelvin Method", Materials Science Forum, vols. 821-823, pp. 273-276 (2015).

Savtchouk, S. et al., "Non-contact Doping Profiling in Epitaxial SiC", Materials Science Forum, vols. 457-460, pp. 755-758 (2004).

Schroeder, D.K., "Charge-Based and Probe Characterization", Semiconductor Material and Device Characterization, (2006), Ch. 9, pp. 523-527.

Verkuil, R.I. et al., "Contactless Silicon Doping Measurements by Means of a Corona-Oxide-Semiconductor (COS) Technique", Extended Abstracts, vol. 88-2, Abstract No. 438, Electrochemical Society Meeting, Chicago, IL (1988), pp. 643-644.

EP Extended European Search Report Issued in European Application No. 16804449.3, dated Feb. 18, 2019, 8 pages.

JP Office Action in Japanese Appln. No. 2018-515182, dated May 19, 2020, 11 pages (with English translation).

* cited by examiner

US 10,969,370 B2

MEASURING SEMICONDUCTOR DOPING USING CONSTANT SURFACE POTENTIAL CORONA CHARGING

TECHNICAL FIELD

This disclosure relates to systems and methods for measuring a semiconductor doping concentration, in particular, using constant surface potential corona charging.

BACKGROUND

Doping a semiconductor with donor or acceptor impurities changes the semiconductor electrical conductivity. As electrical conductivity is generally an important characteristic of a semiconductor material, for quality control purposes, it can be beneficial to measure or monitor a semiconductor doping concentration (e.g., the concentration of doping atoms per volume of the semiconductor) during the production of semiconductor materials and devices. As examples, a manufacturing process can include steps for monitoring the doping concentration of semiconductor wafers sliced from semiconductor crystals, monitoring the doping concentration of thin epitaxial layers grown or deposited on bulk wafers, and monitoring the doping concentration of semiconductors after the performance of deliberate doping processes (e.g., after impurity diffusion or ion implantation processes).

SUMMARY

In general, in an aspect, a method of characterizing a semiconductor sample includes measuring an initial value, $V_{in}$, of a surface potential at a region of a surface of the semiconductor sample, biasing the semiconductor sample to have a target surface potential value ($V_0$) of 2V or less, and depositing a monitored amount of corona charge ($\Delta Q_1$) on the region of the surface after adjusting the surface potential to the target value. The method also includes measuring a first value, $V_1$, of the surface potential at the region after depositing the corona charge, determining the first change of surface potential ($\Delta V_1 = V_1 - V_0$), determining the first capacitance value $C_1 = \Delta Q_1 / \Delta V_1$, and characterizing the semiconductor sample based on $V_0$, $V_1$, $\Delta V_1$, $\Delta Q_1$ and $C_1$.

Implementations of this aspect may include or more of the following features.

In some implementations, the method can further include a series of consecutive monitored corona charge deposition steps with adjustment of the surface potential to the target value ($V_0$) before each deposition step and measuring a surface potential value after each deposition step and using the results of each step to determine corresponding incremental values of surface potential ($\Delta V_k$), corona charge ($\Delta Q_k$), capacitance ($C_k$), and cumulative values of surface voltage ($V_k = \Sigma \Delta V_k$) and charge ($Q_k = \Sigma \Delta Q_k$), where k refers to the $k^{th}$ step, and the semiconductor sample is characterized based on the values for $V_0$, $V_k$, $\Delta V_k$, $Q_k$ and $C_k$. The corona charge $\Delta Q_k$ can be corrected by a calibration function F(V, I) to obtain a charge density ($\Delta Q_{ck}$) under a probe used for measuring the surface potential. $\Delta Q_{ck}$ can be used to determine a corrected space charge capacitance, $C_{ck} = \Delta Q_{ck} / \Delta V_k$. A corrected net corona charge density $Q_{ck} = \Sigma \Delta Q_{ck}$ and the corrected space charge capacitance $C_{ck}$ can be used to determine a doping density of the semiconductor sample from a slope of a $1/C_{ck}^2$ vs. $V_k$ plot, a slope of a $Q_{ck}^2$ vs. $V_k$ plot or from a $C_{ck}Q_{ck}$ capacitance charge factor. A quality of the calibration function can be determined using the capacitance charge factor $C_{ck}Q_{ck}$. The method can further include performing a charge density calibration using a semiconductor calibrating sample with a known doping density over a distance W under a surface of the semiconductor calibrating sample. The corona charge deposition and surface potential adjustment steps can be repeated until a target doping monitoring depth is reached.

In some implementations, a polarity of the corona charging can be such that it creates a depletion surface space charge region in the semiconductor sample. The semiconductor sample can be an n-type semiconductor and the corona charge is deposited using a negative charging polarity. The semiconductor sample can be a p-type semiconductor and the corona charge is deposited using a positive charging polarity.

In some implementations, characterizing the semiconductor sample can include determining a doping density and/or a doping profile.

In some implementations, the semiconductor sample can include a wide bandgap semiconductor.

In some implementations, the semiconductor sample can include a semiconductor selected from the group consisting of SiC, GaN, ZnO, ZnS, and ZnSe.

In some implementations, the surface potential measurements can be performed using a non-contact vibrating probe.

In some implementations, surface potential measurements can be performed using a capacitive electrode.

In some implementations, $V_0$ can be 0.5 V or less.

In some implementations, $V_0$ can be approximately 0 V.

In some implementations, the deposited corona charge can be photo-neutralized and removed from the semiconductor surface using illumination with light of photon energy sufficient to generate excess carriers in the semiconductor sample. The method can further include repeating characterization of the semiconductor sample after photo-neutralizing the deposited corona charge prior to each repetition.

In general, in another aspect, a method includes repeatedly depositing a corona charge at a region of a surface of a sample after biasing a surface potential at the region to have the same target value.

Among other advantages, embodiments may be used to measure the doping concentration of a semiconductor sample without fabricating any permanent or temporary metal-semiconductor diodes and without any invasive electrical contacts. Thus, in some cases, measurements can be obtained relatively quickly, and the semiconductor wafer can be further processed or used after the doping measurement is performed. Further, in some implementations, electrical charges can be deposited onto a surface of a semiconductor sample incrementally and according to a constant compensated surface potential value (e.g., biased to zero or some other constant value), such that the effects of electrostatic charge repulsion are reduced, or in some cases, practically eliminated. Further still, in general, implementations of these techniques can be performed without the use of mercury, a hazardous material that is often subject to environment regulation or other usage restrictions.

The details of one or more embodiments are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1A:
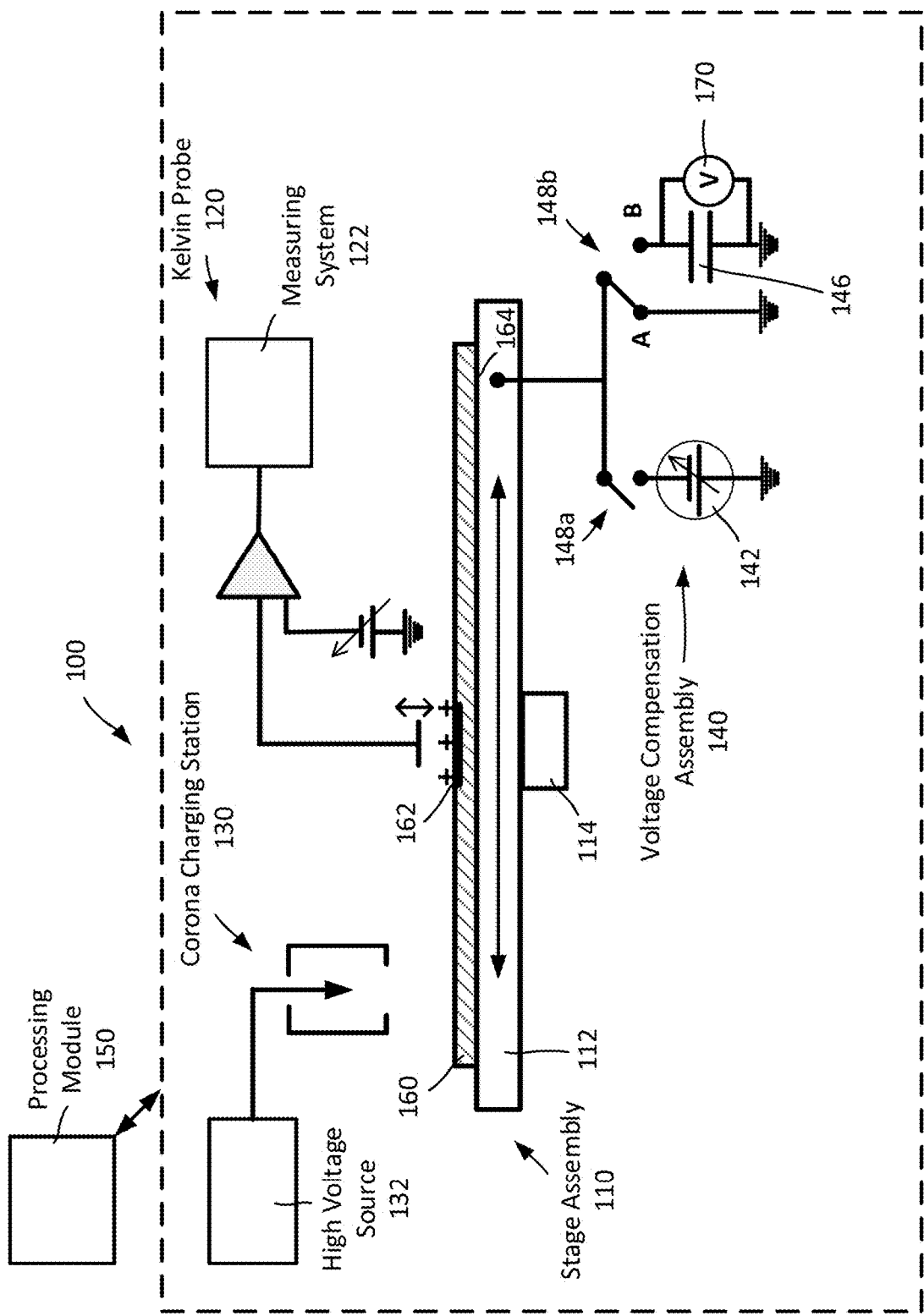
FIG. 1A is a schematic diagram of an example system for measuring doping concentrations of semiconductor samples in a first configuration.

The present disclosure pertains to measuring doping concentrations of a semiconductor using accurate, fast-feedback, non-invasive, and non-contact techniques. Implementations of these techniques include measuring the surface potential at a test site of a semiconductor, applying a bias voltage to the semiconductor in order to obtain a particular surface potential at the test site (e.g., zero, substantially zero, or some other constant value), and depositing a charge on the test site of the semiconductor surface (e.g., using corona discharge in air). This sequence of surface potential measurement, surface potential compensation, and charge deposition can be repeated multiple times in order to create a precisely controlled depletion surface space charge layer, similar to that of a Schottky barrier in metal contact diodes. The semiconductor depletion space charge capacitance C can then be measured to determine the doping concentration of the semiconductor in the depletion space charge layer, and to obtain doping depth profiles beneath the semiconductor surface. In some implementations, the product of the semiconductor depletion space charge capacitance and the total charge deposited at the test site, CQ, can be used as a measurement quality factor for precise doping depth profiling.

As the surface potential of the semiconductor is compensated after each incremental deposition of charge, the effects of electrostatic charge repulsion are reduced, or in some cases, practically eliminated. Further, as the depletion space charge layer can be formed without fabrication of any permanent or temporary metal-semiconductor diodes and without any invasive electrical contacts, measurements can be obtained relatively quickly, and the semiconductor wafer can be further processed or used after the doping measurement is performed. Further, in general, implementations of these techniques can be performed without the use of mercury, a hazardous material that is often subject to environment regulation or other usage restrictions.

Implementations of these techniques can be used to measure doping concentrations of semiconductor materials capable of retaining corona deposited charge. This can include, for example, wide bandgap semiconductors (e.g., SiC, GaN, or ZnO semiconductors that are not exposed to short wavelength illumination). This can also include, for example, semiconductors that have been coated with dielectric films that prevent corona charge neutralization (e.g., $SiO_2$, or $Si_3N_4$ films).

Further, implementations of these techniques can be used to improve the manufacturing of semiconductor wafers used for a variety of applications. For example, these techniques can extend the range of corona-induced depletion voltages to relatively high voltages (e.g., hundreds of volts), which can be advantageous for conducting doping profiling in SiC and GaN semiconductor wafers for high voltage power devices. As another example, these technique can be used to improve the manufacturing of semiconductor wafers that are used for optoelectronic applications.

In some cases, the described techniques also can be applied to other corona charge-based characterization processes, including the measurement of dielectrics and interface on wafers and micro-test sites.

An example system 100 for measuring the doping concentration of a semiconductor sample is shown in FIG. 1A. The system 100 includes a stage assembly 110, a Kelvin probe 120, a corona charging station 130, a voltage compensation assembly 140, and a processing module 150.

In an example operation of the system 100, a semiconductor sample 160 is placed on the stage assembly 110 and is positioned for examination by the Kelvin probe 120. The Kelvin probe 120 measures the surface potential of a test site 162 on the front surface of the semiconductor sample 160. The voltage assembly 140 then applies a bias voltage to the semiconductor sample 160 (e.g., at the back surface 164 of semiconductor sample 160) to compensate the surface potential of the test site to a particular value (e.g., zero volts, 0.5V or less, or some other value). The semiconductor sample 160 is then repositioned beneath the corona charging station 130, which deposits a charge on the test site 162 of the semiconductor sample 160. After the charge is deposited, surface potential measurement, surface potential compensation, and charge deposition are repeated one or more times in order to create a depletion space charge layer that is induced beneath the surface on the semiconductor sample 160 by the deposited charge. After each of these repetitions, the semiconductor depletion space charge capacitance is determined, and based on these determinations, the processing module 150 determines the doping concentration of the semiconductor and/or doping depth profiles beneath the semiconductor surface. During this process, the semiconductor sample 160 can be shielded from stray illumination (e.g., by enclosing all or part of the system 100 in a light-shielded housing or facility).

The stage assembly 110 supports and positions the semiconductor sample 160 during examination by the system 100. The stage assembly 110 includes a chuck 112 capable of conducting electric charge to and from the semiconductor sample (e.g., a semiconductor wafer). In some cases, the chuck 112 can be composed of one or more electrically conductive materials. For example, the chuck 112 can be composed of aluminum, and coated with titanium nitride. In practice, other conductive materials are also possible, depending on the implementation.

The semiconductor sample 160 (e.g., semiconductor wafer) is secured to the chuck 112 such that electrical contact is provided between the semiconductor sample 160 (e.g., the back surface 164) and the chuck 112. The semiconductor sample 160 can be non-invasively secured to the chuck 112. For example, in some cases, the semiconductor sample 160 can be secured to the chuck 112 through suction applied by a vacuum 114. Although a vacuum 114 is shown in FIG. 1A, in practice, other securing mechanisms (e.g., pins, brackets, and/or ties) are also possible, depending on the implementation.

The stage assembly 110 can move along one or more axes, such that the semiconductor sample 160 can be translated in relation to the Kelvin probe 120 and the charging station 130. For example, in some cases, the chuck 112 can move along the x, y, and/or z axes of a Cartesian coordinate system in order to move the semiconductor sample 160 along any of three dimensions in relation to the other components of the system 100.

As shown in FIG. 1A, the stage assembly 110 initially positions the semiconductor sample 160 beneath the Kelvin probe 120, such that the Kelvin probe 120 can measure the surface potential of the test site 162. Measurements obtained by the Kelvin probe 120 are transmitted to the processing module 150 for analysis.

The Kelvin probe 120 can measure the surface potential of the test site 162 without contacting the semiconductor sample 160. The surface potential can be obtained by measuring the constant potential difference (CPD) between a reference probe having a known work function, and the semiconductor surface having an unknown work function. Typically, the probe is placed above the surface of the semiconductor test site and is vibrated, which causes a periodic variation in capacitance between the probe and the semiconductor test site and causes a time-varying current into the probe. This current may be measured and nullified by applying an opposite voltage on the probe or semiconductor surface. This voltage, known as the backing potential, results in zero current when it is equal to the CPD between the probe and the semiconductor surface. This voltage can be determined, for example, using a measuring system 122.

Although a vibrating Kelvin probe 120 is shown in FIG. 1A, in practice, other non-contact vibrating probes or measurement systems also can be used, depending on the implementation. For example, in some cases, a Monroe probe can be used instead of a Kelvin probe In some implementations, the vibrating probe 120 can have a particular diameter (e.g., 1 mm, 2 mm, or some other diameter). In some cases, the Kelvin probe 120 can move with respect to the semiconductor sample (e.g., move laterally across the semiconductor sample) in order to measure the surface potential of several test sites on the semiconductor sample.

During measurement of the surface potential of the test site 162, the voltage compensation assembly 140 is configured to electrically ground the back surface 164 of the semiconductor sample 160. For example, as shown in FIG. 1A, the voltage compensation assembly 140 includes a direct current (DC) voltage source 142 coupled to the chuck 112 through a switch 148a, and an input capacitor 146 coupled the chuck 112 through a switch 148b. During measurement of the surface potential of the test site 162, the switch 148a is open, and the switch 148b is in position A. As a result, the chuck 112 and the back surface 164 of the semiconductor sample 160 are both electrically grounded.

Figure 1B:
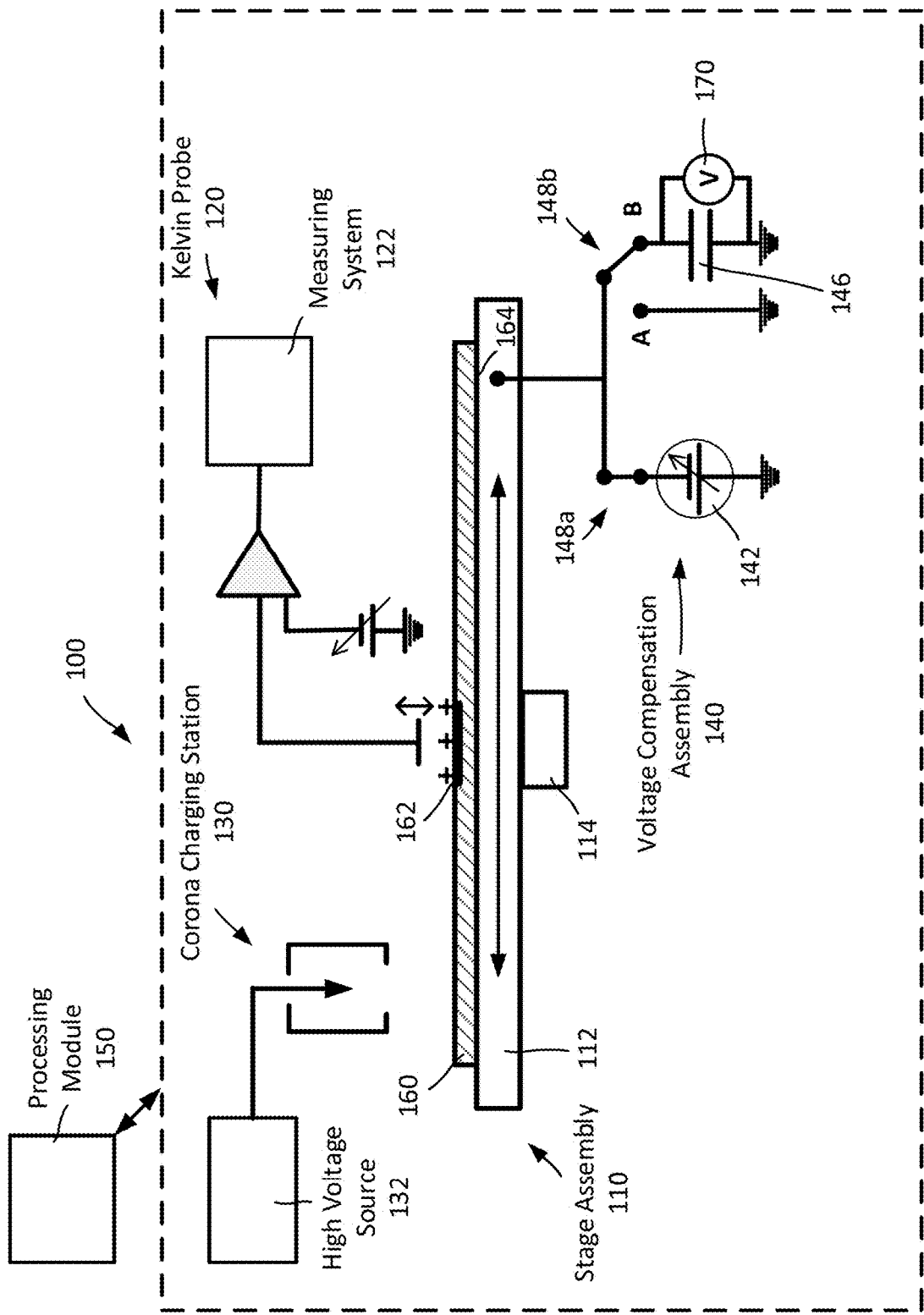
FIG. 1B is a schematic diagram of the example system shown in FIG. 1A in a second configuration.

The system 100 compensates the test site surface potential by applying a bias voltage to the back surface 164 of the semiconductor sample 160. As shown in FIG. 1A, in some implementations, this bias voltage is applied by electrically coupling the input capacitor 146 to the back surface 164 of the semiconductor sample 160, and charging the input capacitor 146 until a particular bias voltage is obtained across it. As shown in FIG. 1B, this can be performed by closing the switch 148a and toggling the switch 148b to position B. When the switches 148a-148b are in these positions, the DC voltage source 142 and the input capacitor 146 are each electrically coupled together and to the chuck 112. Thus, the DC voltage sources 142 electrically charges the input capacitor 146. Further, as the input capacitor 146 is electrically coupled to the chuck 112 and the back surface 164 of the semiconductor sample 160, the voltage across the input capacitor 146 biases the test site surface potential.

The bias voltage of the input capacitor 146 can be monitored using a measuring system 170 in parallel with the input capacitor 146. Measurements obtained by the measuring system 170 can be transmitted to the processing module 150 for analysis.

The DC voltage source 142 can be configured to charge the input capacitor 146 to a particular bias voltage in order to compensate the surface potential at the test site 162. In some cases, the DC voltage source 142 can be configured to achieve a zero, or substantially zero surface potential at the test site 162. For instance, the DC voltage source 142 can charge the input capacitor 146 such that the bias voltage across the input capacitor 146 is the opposite of the surface voltage that was measured by the Kelvin probe 120. That is, if the Kelvin probe 120 measured a surface voltage of $V_0$ while the back surface 164 was electrically grounded (e.g., while the switch 148a was open and the switch 148b was in position A), while the switch 148b is closed and the switch 148b is in position B, the DC voltage source 142 can apply a voltage of $-V_0$ across the input capacitor 146. Thus, the surface potential at the test site 162 is compensated to zero once the input capacitor 146 is charged and a bias voltage of $-V_0$ is obtained across it.

Figure 1C:
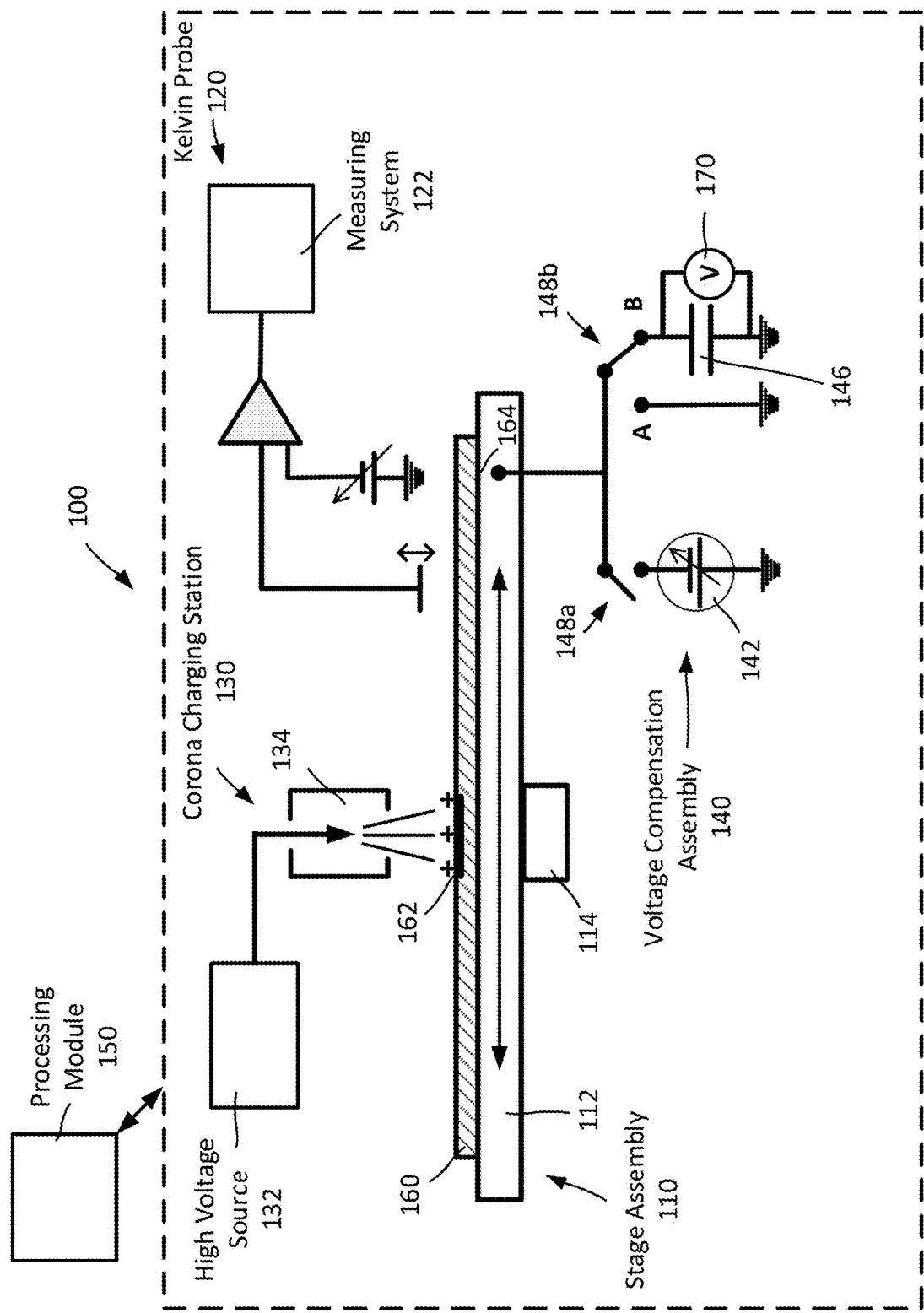
FIG. 1C is a schematic diagram of the example system shown in FIG. 1A in a third configuration.

After the input capacitor 146 is charged, an electrical charge is deposited onto the test site 162 according to the biased surface potential condition. As shown in FIG. 1C, the semiconductor sample 160 is repositioned by the stage assembly 110, such that the test site 162 is positioned beneath the corona charging station 130. The corona charging station 130 then deposits a charge on the test site 162. During charge deposition, the switch 148a is in an open position, and the switch 148b is in position B. Thus, the input capacitor 146 continues to bias the test site's surface potential during charge deposition.

In some cases, the corona charging station 130 deposits charge onto the test site 162 through corona discharge in air. For example, as shown in FIG. 1C, the corona charging station 130 includes a high voltage source 132, and a corona charging gun 134 with a discharge needle electrode. High voltage creates corona discharge and the ions generated by the corona discharge are directed from the charging gun 134 towards the test site 162, and are deposited on the surface of the test site 162. As a result of the charge deposition, a slight change of voltage is induced across the input capacitor 146. This voltage change, $\delta V$, can be used as an in situ measure of the deposited charge $Q_{in}=C_{in}\delta V$, where $C_{in}$ is the capacitance of the input capacitor 146 and $Q_{in}$ is the deposited charge. This change in voltage can be measured using the measuring system 170 in parallel with the input capacitor 146. Measurements obtained by the measuring system 170 can be transmitted to the processing module 150 for analysis.

In some implementations, the corona charging station 130 is configured to deposit charge within a particular region (e.g., a circular region having, e.g., a diameter of approximately 8-10 mm), and the Kelvin probe 120 can be configured to measure the surface potential of a smaller sub-region within the charge deposition region (e.g., a circular sub-region having a diameter of approximately 2 mm). This can be beneficial, for example, to ensure that charge is being uniformly deposited across the entirety of the region being measured by the Kelvin probe 120.

After charge is deposited onto the semiconductor sample 160, the sequence of surface potential measurement, surface potential compensation, and charge deposition shown in FIGS. 1A-1C can be repeated one or more times in order to vary, in a precisely controlled manner, the surface depletion space charge layer at the test site 162. For example, the system 100 can be returned to the configuration shown in FIG. 1A, and a new surface voltage measurement $V_1$ can be determined for the test site 162. Likewise, the system 100 can again be switched to the configuration shown in FIG. 1B, in order to bias the surface potential of the test site 162 according to the new voltage measurement $V_1$ (e.g., by charging the input capacitor 146 to a bias voltage of $-V_1$ and coupling the input capacitor 146 to the back surface 164 of the semiconductor sample 160). Further, the system 100 can again be switched to the configuration shown in FIG. 1C, such that charge can again be deposited onto the test site 162 according to the biased surface potential condition. In this manner, charge can be incrementally deposited onto the test site 162 according to a consistent or substantially consistent surface potential. Further still, the voltage change that is induced during each charge deposition step can be observed and used as an in situ measure of the deposited charge.

The processing module 150 determines the doping concentration of the semiconductor and/or doping depth profiles beneath the semiconductor surface based on the semiconductor depletion space charge capacitance. For example, the voltage difference caused by charging, $\Delta V=V_1-V_0$, and the density of deposited charge, $\Delta Q$ per cm$^2$, can be used to determine the semiconductor space charge capacitance, $C=\Delta Q/\Delta V$. As described in greater detail below, this relationship can be used to estimate the doping concentration of the semiconductor sample.

In some implementations, the processing module 150 can be implemented using digital electronic circuitry, or in computer software, firmware, or hardware, or in combinations of one or more of them. For example, in some cases, the processing module 150 can be implemented, at least in part, as one or more computer programs (e.g., one or more modules of computer program instructions, encoded on computer storage medium for execution by, or to control the operation of, a data processing apparatus). A computer storage medium can be, or can be included in, a computer-readable storage device, a computer-readable storage substrate, a random or serial access memory array or device, or a combination of one or more of them. The term "processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

In some implementations, the processing module 150 can also control the operation one or more of the other components of the system 100. For example, in some implementations, the processing module 150 can be communicatively coupled to the stage assembly 110, the Kelvin probe 120, the corona charging station 130, and/or the voltage compensation assembly 140 in order to control each of these components.

The sequence of surface potential measurement, surface potential compensation, and charge deposition can be repeated any number of times in order to create a particular surface depletion layer. For instance, in some cases, the sequence can be repeated for a prescribed number repetitions (e.g., 10 repetitions, 20 repetitions, 30 repetitions, or any other number of repetitions) or until a desired width of the surface depletion layer W is obtained. In some cases, a larger number of incremental charging steps (e.g., 10 or more, 20 or more) can be used for doping depth profiling and for corona charge calibration.

By incrementally depositing charge in this manner, the capacitance C becomes a differential depletion space charge capacitance $C_D$ related to the width of the surface depletion layer W as $C_D=\varepsilon_s\varepsilon_o/W$, where $\varepsilon_s$ is the dielectric constant of the semiconductor and $\varepsilon_o$ is the permittivity of free space $\varepsilon_o=8.854\times10^{-14}$ F/cm. As an example, an initial surface potential value $V_0$ is determined for a test site on the front surface of semiconductor sample, and the surface potential of the test site is compensated by applying a bias voltage (e.g., $-V_O$) to the back surface of a semiconductor sample. A dose of charge having a charge density $\Delta Q_1$ is then deposited at the test site. After charge deposition, the bias voltage is removed, and the surface potential value $V_1$ is determined for the test site. The differential surface space charge capacitance $C_1$ of the semiconductor sample is then calculated using the relationship $C_1=\Delta Q_1/(V_1-V_0)$. The surface potential of the test site is then compensated by applying a new bias voltage (e.g., $-V_1$) to the semiconductor sample. A second dose of charge having a charge density $\Delta Q_2$ is then deposited at the test site. After charge deposition, the bias voltage is removed, and the surface potential value $V_2$ is determined for the test site. The differential surface space charge capacitance $C_2$ of the semiconductor sample is then calculated using the relationship $C_2=\Delta Q_2/(V_2-V_1)$.

This sequence can be repeated k number of times (e.g., k=20 repetitions) or until achieving a desired doping monitoring depth $W=\varepsilon_s\varepsilon_o/C_k$. For example, in some cases, a series of consecutive monitored corona charge deposition steps can be performed, and the surface potential at the test site can be adjusted to a particular target value (e.g., zero volts, 0.5 V or less, or some other value) before each deposition step. The surface potential value can be measured after each deposition step, and the measurement results of each step can be used to determine corresponding incremental values of surface potential ($\Delta V_k$), corona charge ($\Delta Q_k$), capacitance ($C_k$), cumulative values of surface voltage ($V_k=\Sigma\Delta V_k$) and charge ($Q_k=\Sigma\Delta Q_k$), where k refers to the $k^{th}$ step or repetition. The semiconductor sample can be characterized based on the values for $V_0$, $V_k$, $\Delta V_k$, $Q_k$ and $C_k$.

In some cases, the deposited charge density doses can be the same for each repetition of charge deposition (e.g., $\Delta Q_1=\Delta Q_2=\Delta Q_3=\ldots=\Delta Q_k$).

In some implementations, the deposited charge can be removed after the doping concentration of the semiconductor is determined. For example, in some cases, corona deposited charge can be photo-neutralized and removed from the semiconductor surface using illumination with photon light energy sufficient to generate excess carriers in a semiconductor sample (e.g., blue light having photon energy above 3.3 eV for SiC, GaN or ZnO semiconductors). In some cases, the doping concentration of a test site can be measured multiple times by removing deposited charges between each measurement, and repeating the deposition of charge.

Measuring the doping concentration of a semiconductor often requires a particular depletion barrier voltage (e.g., 10V, 20V, 50V, 100V, 200V or more). Without compensation, high surface potentials can often hinder corona charge deposition due to the electrostatic forces that exist between the deposited and incoming corona ions. For example, in some cases, electrostatic repulsion between the deposited and incoming corona ions can limit the density of charge deposition. In addition, in many cases, the forces acting on corona ions can direct incoming ions away from the center of the charging site, causing non-uniform lateral distribution of charge density. This potentially can cause errors in the quantification of deposited charge dose density at the test site, and can cause corresponding errors in capacitance and doping density calculations. These limitations and errors can be mitigated or, in some cases, entirely eliminated by incrementally depositing charge onto a semiconductor surface having a constant or substantially constant surface potential at the deposition site (e.g., in the manner described above).

When measuring semiconductor doping concentration using corona charge-based techniques, the surface depletion layer is created due to net electrical neutrality of the semiconductor surface and the underlying surface space charge region. Accordingly, an electric charge placed on the semiconductor surface is mirrored by the opposite charge in the surface space charge region. To create depletion-type space charge, negative corona charge is deposited on an n-type semiconductor and positive corona charge is deposited on a p-type semiconductor.

For semiconductor doping concentration N, the depletion layer space charge per unit area can be expressed as $Q_D=qNW$, where W is the depletion layer width and q is the elemental charge. The depletion layer forms a capacitor with the capacitance $C_D$ per unit area:

$$C_D = \frac{\varepsilon_S \varepsilon_o}{W} = q\frac{\varepsilon_S \varepsilon_o}{Q_D}N$$

Based on the above relation, a doping measurement can be obtained based on the capacitance times charge factor CQ. This can used for two purposes: i) for calibration of corona deposited charge density Q, and ii) for determination of the doping concentration N.

Corona charge calibration can be used to precisely determine the incremental charge density ΔQ deposited per unit surface area at the test site. By compensating the surface potential of a semiconductor test site and depositing charge at the test site according to constant compensated surface potential, the surface of the semiconductor can be charged more precisely and/or more uniformly.

Further, in some cases, in situ measured charge increments $\Delta Q_{ink}$ (e.g., $\Delta Q_{in1}$, $\Delta Q_{in2}$, or any other value $\Delta Q_{ink}$, as described above) can be converted into calibrated charge increments at the test site $\Delta Q_{ck}=Q_{in}F(V, I)$, where F(V, I) is a calibration function dependent on the surface potential V and I is the corona charging current. The calibrated charge increments $\Delta Q_{ck}$ can be used to determine a corrected space charge capacitance $C_{ck}=\Delta Q_{ck}/\Delta V_k$, which in turn can be used to determine a corrected doping concentration. In some cases, the calibration function F(V, I) can be determined empirically. For example, a charge density calibration can be performed using a semiconductor calibrating sample having a known doping density with a constant doping depth profile over a known distance W under the surface. The function F(V, I) can be determined by determining a corrective function needed to satisfy the relationship $\Delta Q_{ck}=\Delta Q_{in}F(V, I)$. This function can then be used to correct doping density determinations for samples having unknown doping densities.

A number of different techniques can be used to calculate the doping density using the corrected corona charge increments $\Delta Q_{ck}$, the measured change in surface voltage, $\Delta V_k$, and the corrected space charge capacitance $C_{ck}=\Delta Q_{ck}/\Delta V_k$. As an example, in some cases, a $1/C^2$–V technique can be used. By analogy to a Schottky diode C–V measurement, the calculation of doping density N can be made using a plot of $1/C_{ck}^2$ versus the surface voltage $V_k$ based on the follow relationship, where the corrected space charge capacitance $C_{ck}$ can be used in place of C:

$$\frac{1}{C_{ck}^2} = \frac{2(V_k - V_o)}{q\varepsilon_S \varepsilon_o N}$$

If the doping density is constant through the depletion region, the plot is a straight line and the doping density is determined from the slope of the line as:

$$N = \frac{2}{\varepsilon_S \varepsilon_o}(slope^{-1})$$

Figure 2:
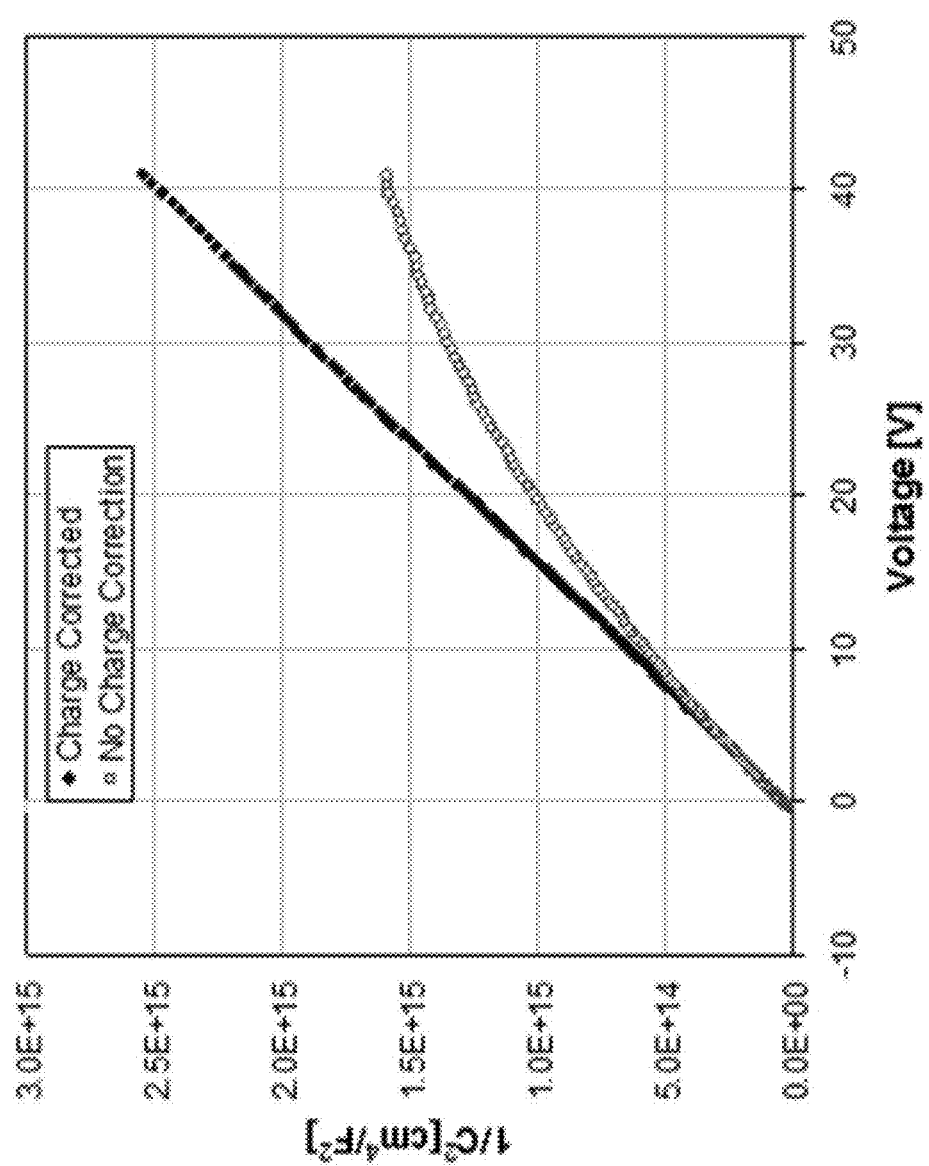
FIG. 2 is an example $1/C^2$ vs. V plot with and without corona charge areal density correction for a very uniformly doped p-type epitaxial SiC semiconductor sample with $N=2.37\times10^{17}$ cm$^{-3}$.

FIG. 2 illustrates an example $1/C^2$ vs. V plot with and without corona charge areal density correction for a very uniformly doped p-type epitaxial SiC semiconductor sample with $N=2.37\times10^{17}$ cm$^{-3}$. In this example, without the correction, erroneous bending of the line is observed. In some cases, a very large overestimation of N up to 50% can be made in higher voltage range by using uncorrected corona charge. For example, in some cases, a need for charge correction can be apparent for surface voltages exceeding about 8V. This effect demonstrates the importance of electrostatic force effects in corona-charging, even for relatively low surface potentials.

As another example, another technique that can be used to assess the doping concentration N is the $Q^2$–V technique. For example, the doping density N can be determined based on the total charge $Q_k$, the total surface voltage $V_k$, and the depletion layer relationship, where the corrected corona charge increments $\Delta Q_{ck}$ can be used to determine the total charge $Q_{ck}=\Sigma Q_{ck}$:

$$Q_{ck}^2 = 2q\varepsilon_s\varepsilon_o N|V_k - V_o|$$

If N is constant, this $Q^2$–V equation gives a straight line, and the slope of this straight line gives the doping concentration N:

$$N = \frac{1}{2q\varepsilon_S\varepsilon_o} \cdot |(slope)|$$

In some cases, the cumulative total charge used in the $Q^2$–V technique can be more sensitive to charge dose errors and to corresponding corona charge neutralization by leakage current, compared to a single charge increment $\Delta Q_{ck}$ used in the capacitance measurement and the $1/C^2$–V technique. In cases of negligible leakage and proper correction of charge dose for electrostatic force effect, both techniques can provide similar results.

Figure 3:
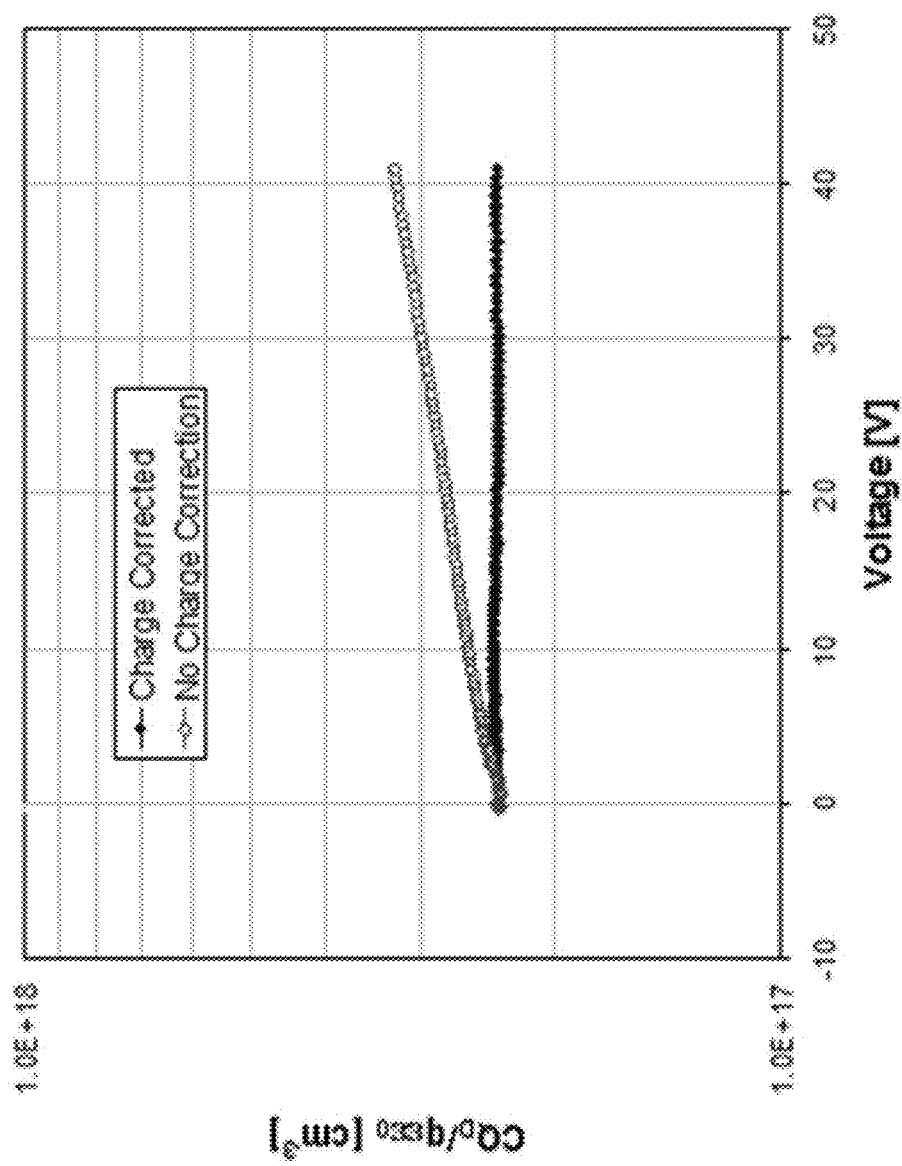
FIG. 3 is an example CQ vs. V plot for very uniformly doped p-type epitaxial SiC with $N=2.37\times10^{17}$ cm$^{-3}$ with and without corona charge correction.

The capacitance-charge product, CQ, of a semiconductor (or $C_{ck}Q_{ck}$ if expressed according to the corrected space charge capacitance and the corrected corona charge increment) also can be used to determine the doping concentration N. FIG. 3 illustrates this CQ factor (where CQ is proportional to N) as a function of surface voltage with and without corona charge correction for an example constant doping density p-type epitaxial SiC semiconductor sample with $N=2.37 \times 10^{17}$ cm$^{-3}$. In this example, at 40V, the error in N is about 35% by not using corrected corona charge. The CQ factor can be a constant for a sample with a uniform dopant depth profile (e.g., as illustrated in FIG. 3), and in these cases, can be used as a self-consistent charge dose verification metric. For example, semiconductors having non-uniform dopant depth profile can be distinguished by identifying semiconductors exhibiting a varying or non-constant CQ profile.

Figure 4:
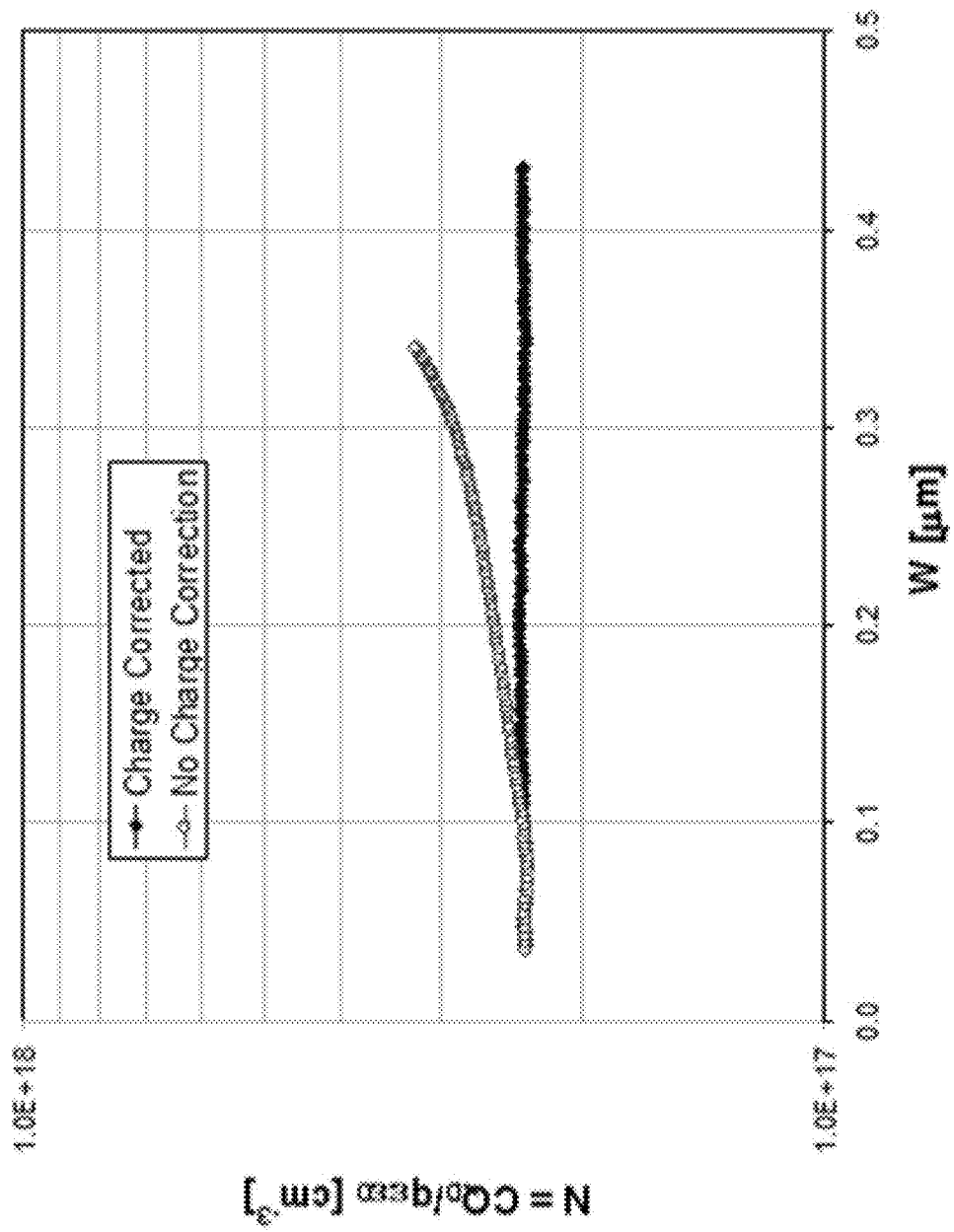
FIG. 4 is a dopant depth profile for an example p-type epitaxial SiC semiconductor sample with constant doping density $N=2.37\times10^{17}$ cm$^{-3}$ determined using the CQ factor with and without corona charge correction.

As another example, FIG. 4 illustrates the dopant depth profile for an example p-type epitaxial SiC semiconductor sample with constant doping density $N=2.37 \times 10^{17}$ cm$^{-3}$ determined using the CQ factor with and without corona charge correction. As shown in FIG. 4, due to the uniform dopant depth profile of the sample, the corrected CQ factor is substantially constant.

Figure 5:
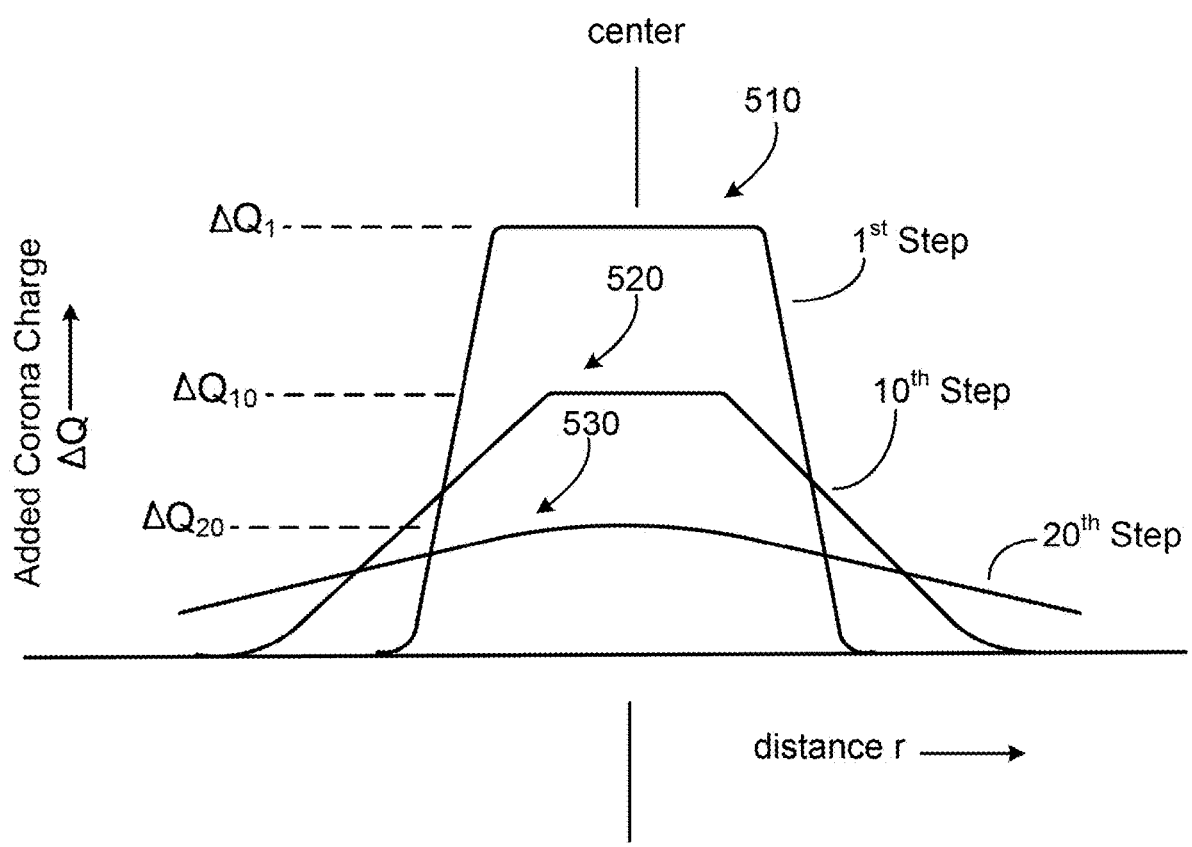
FIG. 5 shows example charge profiles for a semiconductor wafer after an initial deposition of charge, after a sequence of ten depositions of charge, and after a sequence of twenty depositions of charge.

Depositing charge following a surface potential adjustment to constant value can eliminate or otherwise reduce undesirable charge deposition patterns that tend to occur over multiple charging steps at the same site, such as the presence of craters, gradients, or other non-uniform charge deposition patterns. As a comparative example, FIG. 5 shows charge profiles for a semiconductor wafer after an initial deposition of charge (profile 510) nominally at a center location on a surface, after a sequence of ten depositions of charge (profile 520) at the same location, and after a sequence of twenty depositions of charge (profile 530) at the same location. In this example, the surface potential of the semiconductor wafer was not adjusted to a constant target value prior to each deposition of charge. As a result, electrostatic repulsion causes a decrease of the charge magnitude at the center and a spreading of the charge profile is observed at the deposition site after successive charge depositions. In contrast, by adjusting (biasing) the surface potential prior to each charge step, the spread of the charge profile can be lessened and the space-charge profile remains similar from one charging to the next. Accordingly, the accuracy of charge deposition and corona charge monitoring can be improved.

Although an example system 100 is shown and described, this is merely an illustrative example. In practice, the system 100 can have other arrangements, depending on the implementation.

For example, in some cases, the stage assembly 110 does not move during doping concentration measurement. Instead, one or more of the other components of the system 100 (e.g., the Kelvin probe 120 and/or the corona charging station 130) can move with respect to the semiconductor sample 160 in order to perform doping concentration measurements.

Figure 6:
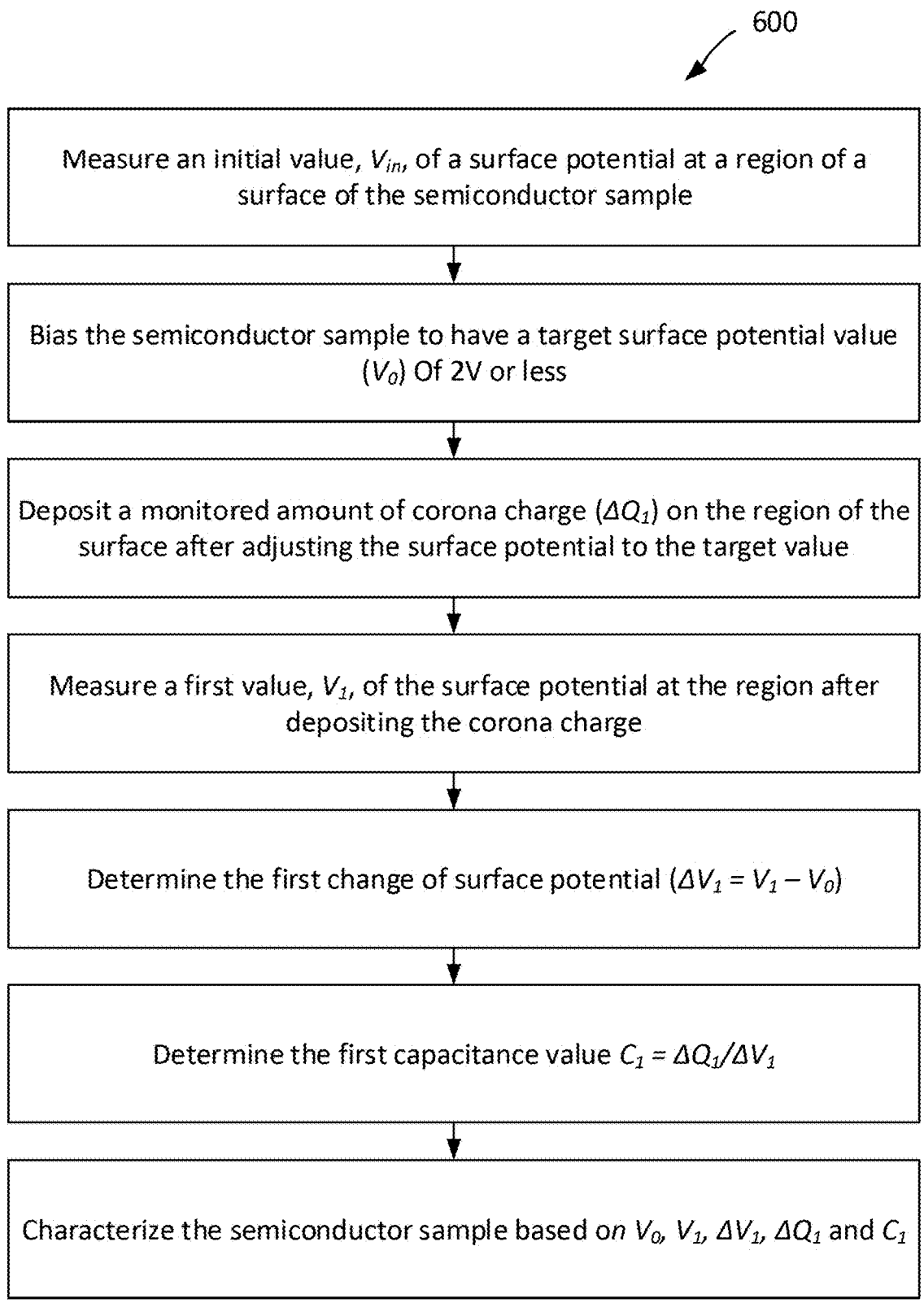
FIG. 6 shows an example method of characterizing a semiconductor sample.

FIG. 6 shows an example method 600 of characterizing a semiconductor sample.

Figure 7:
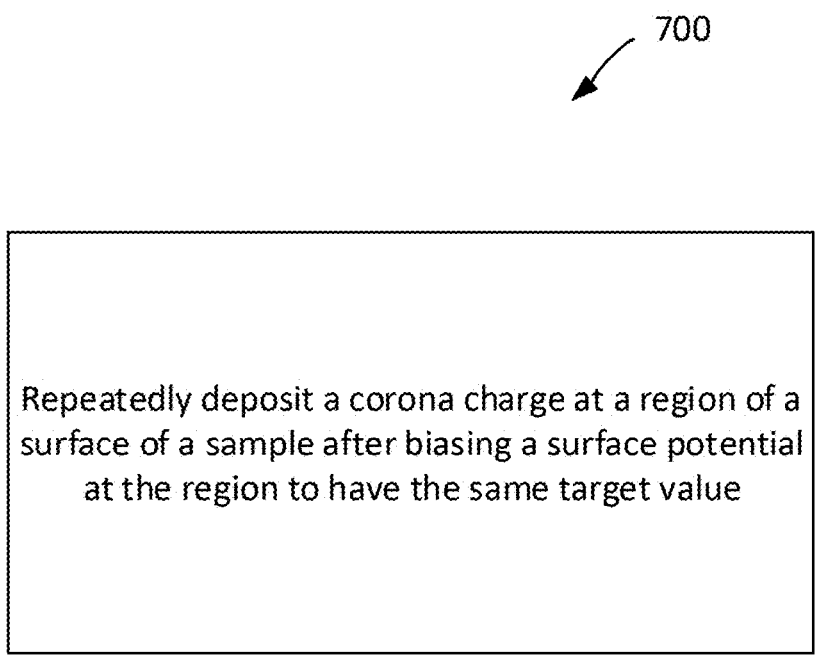
FIG. 7 shows an example method of depositing a corona charge at a region of a surface of a sample.

FIG. 7 shows an example method 700 of depositing a corona charge at a region of a surface of a sample.

A number of embodiments have been described. Nevertheless, it will be understood that various modifications may be made without departing from the spirit and scope of the disclosure. Accordingly, other embodiments are within the scope of the following claims.

What is claimed is:

1. A method of characterizing a semiconductor sample, the method comprising:
   (i) measuring an initial value of a surface potential at a region of the semiconductor sample;
   (ii) applying a bias voltage to the semiconductor sample via a voltage source electrically coupled to a surface of the semiconductor sample so that the semiconductor sample has a target surface potential value of two volts or less;
   (iii) depositing a dose of corona charge on the region of the surface while applying the bias voltage to the semiconductor sample, wherein the amount of corona charge is monitored during the deposition;
   (iv) measuring a further value of the surface potential at the region after depositing the dose of corona charge and removing the bias voltage from the semiconductor sample;
   (v) determining an incremental value of surface potential equal to a difference between the values of the surface potential, without the bias voltage applied to the semiconductor sample, measured before and after depositing the dose of corona charge;
   (vi) determining a surface space charge capacitance value of the semiconductor sample equal to a ratio of the dose of corona charge to the incremental value of the surface potential;
   (vii) repeating steps (ii) through (vi) k times to provide k corona charge values, k incremental values of surface potential, and k surface space charge capacitance values, wherein k is an integer greater than 1 and sufficient to achieve a target doping monitoring depth of the semiconductor sample; and
   (viii) characterizing the semiconductor sample based on the initial value of the surface potential, the k further values of the surface potential, the k corona charge doses, the k incremental values of the surface potential, and the k surface space charge capacitance values.

2. The method of claim 1, wherein the k corona charge doses are corrected by a calibration function F(V, I) to obtain k corresponding charge density values under a probe used for measuring the surface potential.

3. The method of claim 2, where each of the k charge density values are used to determine a corresponding corrected space charge capacitance equal to a ratio of the corresponding charge density value to the corresponding incremental value of the surface potential.

4. The method of claim 3, where a corrected net corona charge density equal to a sum of the k charge density values and the corrected space charge capacitances are used to determine a doping density of the semiconductor sample.

5. The method of claim 4, wherein a quality of the calibration function is determined using a capacitance charge factor equal to a product of the corrected space charge capacitance and the corresponding corrected net charge density value.

6. The method of claim 1, further comprising performing a charge density calibration using a semiconductor calibrating sample with a known doping density over a distance W under a surface of the semiconductor calibrating sample.

7. The method of claim 1, wherein a polarity of the corona charging is such that it creates a depletion surface space charge region in the semiconductor sample.

8. The method of claim 7, wherein the semiconductor sample is an n-type semiconductor and the corona charge is deposited using a negative charging polarity.

9. The method of claim 7, wherein the semiconductor sample is a p-type semiconductor and the corona charge is deposited using a positive charging polarity.

10. The method of claim 1, wherein characterizing the semiconductor sample comprises determining a doping density and/or a doping profile.

11. The method of claim 1, wherein the semiconductor sample comprises a wide bandgap semiconductor.

12. The method of claim 1, wherein the semiconductor sample comprises a semiconductor selected from the group consisting of SiC, GaN, ZnO, ZnS, and ZnSe.

13. The method of claim 1, wherein the surface potential measurements are performed using a non-contact vibrating probe.

14. The method of claim 1, wherein the surface potential measurements are performed using a capacitive electrode.

15. The method of claim 1, wherein the target surface potential is 0.5 volts or less.

16. The method of claim 1, wherein the target surface potential is approximately zero volts.

17. The method of claim 1, wherein the deposited corona charge is photo-neutralized and removed from the semiconductor surface using illumination with light of photon energy sufficient to generate excess carriers in the semiconductor sample.

18. The method of claim 17, further comprising repeating characterization of the semiconductor sample after photo-neutralizing the deposited corona charge prior to each repetition.

* * * * *